US009061954B2

(12) United States Patent
Minoux et al.

(10) Patent No.: US 9,061,954 B2
(45) Date of Patent: Jun. 23, 2015

(54) DEHYDRATION OF ALCOHOLS ON CRYSTALLINE SILICATES

(75) Inventors: Delphine Minoux, Nivelles (BE);
Nikolai Nesterenko, Nivelles (BE);
Walter Vermeiren, Houthalen (BE);
Sander Van Donk, Sainte-Adresse (FR);
Jean-Pierre Dath, Beloeil Hainaut (BE)

(73) Assignee: TOTAL RESEARCH & TECHNOLOGY FELUY, Seneffe (Feluy) (BE)

( * ) Notice: Subject to any disclaimer, the term of this patent is extended or adjusted under 35 U.S.C. 154(b) by 674 days.

(21) Appl. No.: 12/864,966

(22) PCT Filed: Feb. 5, 2009

(86) PCT No.: PCT/EP2009/051329
§ 371 (c)(1),
(2), (4) Date: Feb. 1, 2011

(87) PCT Pub. No.: WO2009/098262
PCT Pub. Date: Aug. 13, 2009

(65) Prior Publication Data
US 2011/0124939 A1    May 26, 2011

(30) Foreign Application Priority Data

Feb. 7, 2008 (EP) .................................... 08151146
Apr. 11, 2008 (EP) .................................... 08154404

(51) Int. Cl.
*C07C 1/20* (2006.01)
*C07C 1/24* (2006.01)
*B01J 29/40* (2006.01)

(52) U.S. Cl.
CPC .. *C07C 1/24* (2013.01); *B01J 29/40* (2013.01);
*B01J 2229/16* (2013.01); *B01J 2229/36*
(2013.01); *B01J 2229/37* (2013.01); *B01J 2229/42* (2013.01); *C07C 2529/40* (2013.01)

(58) Field of Classification Search
CPC ............ B01J 29/18; B01J 29/40; B01J 29/65;
B01J 29/85; B01J 37/10; B01J 37/28; B01J
2029/08; B01J 2029/81; B01J 2229/18;
B01J 2229/36; B01J 2229/37
USPC .......... 585/634, 638–640; 502/60, 73, 85, 78,
502/79; 423/714
See application file for complete search history.

(56) References Cited

U.S. PATENT DOCUMENTS 4,232,179 A    11/1980 Valladares Barrocas et al.

| 5,171,921 A * | 12/1992 | Gaffney et al. ............... 585/653 |
| 2003/0078463 A1* | 4/2003 | Martens et al. ............... 585/638 |
| 2006/0149109 A1* | 7/2006 | Ruziska et al. ............... 585/639 |
| 2006/0235251 A1* | 10/2006 | Dath et al. .................... 585/639 |
| 2009/0216058 A1* | 8/2009 | Dath et al. .................... 585/653 |
| 2010/0222203 A1 | 9/2010 | Baba et al. |

FOREIGN PATENT DOCUMENTS

| EP | 0123449 A1 | 10/1984 |
| JP | 2005-104912 A1 | 4/2005 |
| JP | 2007-290991 A1 | 8/2007 |
| WO | 99/51548 | 10/1999 |
| WO | WO 2007068734 A1 * | 6/2007 |
| WO | 2007/114195 A1 | 11/2007 |

OTHER PUBLICATIONS

Takahara, I., Saito, M., Inaba, M., and Murata, K., Dehydration of ethanol into ethylene over solid acid catalysts, Catalysis Letters vol. 105, Nos. 3-4, Dec. 2005, pp. 249-252.*
Office Action issued in Chinese Patent Application No. 200980104294.X, dated Jul. 25, 2014 (16 pages).
Office Action issued in European Patent Application No. 09709286.0-1360, dated Jun. 27, 2014 (5 pages).
Ronghou Liu, et al., "Preparation Process of Fuel Ethanol and Examples", Chemical Industry Press, Jan. 2008, pp. 272-274, ISBN: 978-7-122-1396-5.

* cited by examiner

*Primary Examiner* — In Suk Bullock
*Assistant Examiner* — Philip Louie

(57) ABSTRACT

The present invention relates to a process for the dehydration of at least an alcohol to make at least an olefin, comprising:
introducing in a reactor a stream (A) comprising at least an alcohol, optionally water, optionally an inert component, contacting said stream with a catalyst in said reactor at conditions effective to dehydrate at least a portion of the alcohol to make an olefin,
recovering from said reactor an olefin containing stream (B),
Wherein
the catalyst is:
  a crystalline silicate having a ratio Si/Al of at least about 100, or
  a dealuminated crystalline silicate, or
  a phosphorus modified zeolite,
the WHSV of the alcohols is at least 2 h$^{-1}$,
the temperature ranges from 280° C. to 500° C.
It relates also to the same process as above but wherein the catalyst is a phosphorus modified zeolite and at any WHSV. The partial pressure of the alcohol in the dehydration reactor advantageously ranges from 1.2 to 4 bars absolute (0.12 MPa to 0.4 MPa), the temperature of the dehydration reactor ranges advantageously from 300° C. to 400° C. and the alcohol is selected among ethanol, propanol, butanol and phenylethanol.

12 Claims, 14 Drawing Sheets

DEHYDRATION OF ALCOHOLS ON CRYSTALLINE SILICATES

FIELD OF THE INVENTION

Figure 1:
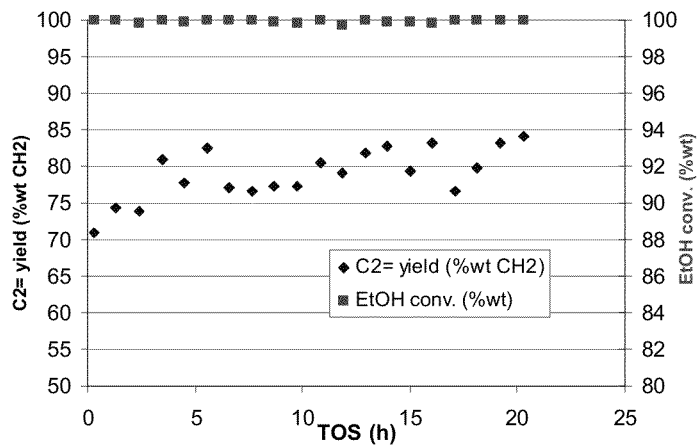

The present invention relates to the dehydration of at least an alcohol on crystalline silicates or modified zeolites to make at least an olefin. The limited supply and increasing cost of crude oil has prompted the search for alternative processes for producing hydrocarbon products such as ethylene. Ethanol can be obtained by fermentation of carbohydrates. Made up of organic matter from living organisms, biomass is the world's leading renewable energy source.

BACKGROUND OF THE INVENTION

U.S. Pat. No. 4,207,424 describes a process for the catalytic dehydration of alcohols to form unsaturated organic compounds in which an alcohol is dehydrated in the presence of alumina catalysts which are pre-treated with an organic silylating agent at elevated temperature. Example 12 relates to ethanol, the WHSV is 1.2 $h^{-1}$ and shows only a conversion increase by comparison with the same alumina but having not been pretreated.

U.S. Pat. No. 4,302,357 relates to an activated alumina catalyst employed in a process for the production of ethylene from ethanol through a dehydration reaction. In the description LHSV of ethanol is from 0.25 to 5 $h^{-1}$ and preferably from 0.5 to 3 $h^{-1}$. The examples are carried out at 370° C. and LHSV of 1 $h^{-1}$, ethylene yield is from 65 to 94%.

Process Economics Reviews PEP' 79-3 (SRI international) of December 1979 describes the dehydration of an ethanol-water (95/5 weight %) mixture on a silica-alumina catalyst in a tubular fixed bed at 315-360° C., 1.7 bar absolute and a WHSV (on ethanol) of 0.3 $h^{-1}$. The ethanol conversion is 99% and the ethylene selectivity is 94.95%. It also describes the dehydration of an ethanol-water (95/5 weight %) mixture on a silica-alumina catalyst in a fluidized bed at 399° C., 1.7 bar absolute and a WHSV (on ethanol) of 0.7 $h^{-1}$. The ethanol conversion is 99.6% and the ethylene selectivity is 99.3%.

U.S. Pat. No. 4,232,179 relates to the preparation of ethylene, based on a process for dehydrating ethyl alcohol. More particularly, the object of said prior art is the production of ethylene in the presence of catalysts, using adiabatic reactors and a high temperature. Such adiabatic reactors may be used in parallel or may be arranged in series or arranged in assemblies of parallel series, or still only a single reactor may be used. The ratio between the sensible heat carrying stream and the feed may range from 0.2:1 to 20:1, but preferably shall be comprised within the range from 0.2:1 to 10:1. On the other hand the space velocity may range between 10 and 0.01 g/h of ethyl alcohol per gram of catalyst, depending on the desired operation severity, the range between 1.0 and 0.01 g/h/g being particularly preferred. In the examples the catalysts are silica alumina, the WHSV on ethanol is from 0.07 to 0.7, the ratio of steam to ethanol is from 3 to 5.

EP 22640 relates to improved zeolite catalysts, to methods of producing such catalysts, and to their use in the conversion of ethanol and ethylene to liquid and aromatic hydrocarbons, including the conversion of ethanol to ethylene. More particularly this prior art relates to the use of zeolite catalysts of Si/Al ratio from 11 to 24 (in the examples) such as the ZSM and related types in the conversion reaction of aqueous and anhydrous ethanol to ethylene, of aqueous ethanol to higher hydrocarbons, and of ethylene into liquid and aromatic hydrocarbons. WHSV ranges from 5.3 to 6 $h^{-1}$, in dehydration to ethylene the reactor temperature is from 240 to 290° C.

U.S. Pat. No. 4,727,214 relates to a process for converting anhydrous or aqueous ethanol into ethylene wherein at least one catalyst of the crystalline zeolite type is used, said catalyst having, on the one hand, channels or pores formed by cycles or rings of oxygen atoms having 8 and/or 10 elements or members. In the examples the atomic ratio Si/Al is from 2 to 45, the temperature from 217 to 400° C. and the WHSV 2.5 $h^{-1}$.

U.S. Pat. No. 4,847,223 describes a catalyst comprising from 0.5 to 7% by weight of trifluoromethanesulfonic acid incorporated onto an acid-form pentasil zeolite having a Si/Al atomic ratio ranging from 5 to 54 and a process for producing same. Also within the scope of said prior art is a process for the conversion of dilute aqueous ethanol to ethylene comprising: flowing said ethanol through a catalyst comprising from 0.5 to 7% by weight of trifluoromethanesulfonic acid incorporated onto an acid-form pentasil zeolite having a Si/Al atomic ratio range from 5 to 54 at a temperature ranging from 170° to 225° C. and recovering the desired product. The WHSV is from 1 to 4.5 $h^{-1}$. The zeolites which are directly concerned by said prior art belong to the family called ZSM or pentasil zeolite family namely ZSM-5 and ZSM-11 type zeolites.

U.S. Pat. No. 4,873,392 describes a process for converting diluted ethanol to ethylene which comprises heating an ethanol-containing fermentation broth thereby to vaporize a mixture of ethanol and water and contacting said vaporized mixture with a ZSM-5 zeolite catalyst selected from the group consisting of:

a ZSM-5 zeolite having a Si/Al atomic ratio of from 5 to 75 which has been treated with steam at a temperature ranging from 400 to 800° C. for a period of from 1 to 48 hours;

a ZSM-5 zeolite having a Si/Al atomic ratio of from 5 to 50 and wherein La or Ce ions have been incorporated in a weight percentage of 0.1 to 1.0% by ion exchange or in a weight percentage ranging from 0.1 to 5% by impregnation, and a ZSM-5 zeolite having a Si/Al of from 5 to 50 and impregnated with a 0.5 to 7 wt % of trifluoromethanesulfonic acid, and recovering the ethylene thus produced.

In ex 1 the catalyst is a steamed ZSM-5 having a Si/Al ratio of 21, the aqueous feed contains 10 w % of ethanol and 2 w % of glucose, the temperature is 275° C., the WHSV is from 3.2 to 38.5 $h^{-1}$. The ethylene yield decreases with the increase of WHSV. The ethylene yield is 99.4% when WHSV is 3.2 $h^{-1}$ and 20.1% when WHSV is 38.5 $h^{-1}$.

In ex 2 a ZSM-5 having a Si/Al ratio of 10 is compared with the same but on which La or Ce ions have been incorporated. The aqueous feed contains 10 w % of ethanol and 2 w % of glucose, the temperature is from 200° C. to 225° C., the WHSV is 1 $h^{-1}$ and the best ethylene yield is 94.9%.

In ex 3 the catalyst is a ZSM-5 having a Si/Al ratio of 10 on which trifluoromethanesulfonic acid has been incorporated, the aqueous feed contains 10 w % of ethanol and 2 w % of glucose, the temperature is from 180° C. to 205° C., the WHSV is 1 $h^{-1}$. The ethylene yield increases with temperature (73.3% at 180° C., 97.2% at 200° C.) and then decreases (95.8% at 205° C.).

U.S. Pat. No. 4,670,620 describes ethanol dehydration to ethylene on ZSM-5 catalysts. In a preferred embodiment the catalysts used according to this prior art are of the ZSM-5 type and preferably at least partially under hydrogen form. In the examples the catalyst is a ZSM-5 or a ZSM-11 having a SI/Al ratio of 40 to 5000 (ex 13), the LHSV is from 0.1 to 1.8 $h^{-1}$ and the temperature from 230° C. to 415° C.

JP 2007-290991 A1 describes the conversion at 500° C. of an ethanol dimethylether mixture on a P—$ZrO_2$/ZSM-5 and W—$ZrO_2$/ZSM-5 to make a mixture of ethylene, propylene and butene.

EP 1396481 describes a process for converting a hydrocarbon feedstock to provide an effluent containing light olefins, the process comprising passing a hydrocarbon feedstock containing at least one C1 to C4 aliphatic hetero compound selected from alcohols, ethers, carbonyl compounds and mixtures thereof through a reactor containing a crystalline silicate catalyst to produce an effluent including propylene, the crystalline silicate being selected from at least one of an MFI-type crystalline silicate having a silicon/aluminium atomic ratio of at least 180 and an MEL-type crystalline silicate having a silicon/aluminium atomic ratio of from 150 to 800 which has been subjected to a steaming step. In the examples only methanol is used, the reaction temperature is between 400 and 550° C. and the effluent is a mixture of ethylene, propylene, C4 olefins, C5 olefins and aromatics.

U.S. Pat. No. 3,911,041 relates to a process wherein methanol and dimethyl ether are converted to a reaction product containing olefins. The conversion is carried out employing a catalyst comprising a crystalline aluminosilicate zeolite having a silica to alumina ratio of at least about 12, a constraint index of about 1 to 12, and containing phosphorus incorporated with the crystal structure thereof in an amount of at least about 0.78 percent by weight. Only methanol and dimethylether are used in the examples. This conversion is similar to the one described in the above EP 1396481 except the catalyst.

It has now been discovered that the dehydration of at least an alcohol to at least an olefin can be made:
on a crystalline silicate having a high Si/Al ratio at least 100 or
on a dealuminated crystalline silicate or
on a phosphorus modified zeolite and
with a WHSV of at least 2 $h^{-1}$.

By way of example, in the dehydration of ethanol on a crystalline silicate having a high Si/Al ratio at least 100 and with a WHSV of at least 4 $h^{-1}$ to make ethylene, the ethanol conversion is at least 98% and often 99%, advantageously the ethylene yield is at least 97%, the ethylene selectivity is at least 96% and often 97% and the ethylene purity is at least 99% and often 99.8%.

The ethanol conversion is the ratio (ethanol introduced in the reactor−ethanol leaving the reactor)/(ethanol introduced in the reactor).

The ethylene yield is the ratio, on carbon basis, (ethylene leaving the reactor)/(ethanol introduced in the reactor).

The ethylene selectivity is the ratio, on carbon basis, (ethylene leaving the reactor)/(ethanol converted in the reactor).

The ethylene purity is the ratio, on carbon basis, (ethylene leaving the reactor)/(ethylene+ethane leaving the reactor). It means the ethylene purity is the percentage of ethylene, on a carbon basis, present in the $C_2$ cut, containing close-boiling compounds, recovered in the stream leaving the reactor. The $C_2$ cut doesn't comprise the unconverted ethanol and acetaldehyde if any. The same definitions apply mutatis mutandis to the alcohol and the olefin.

BRIEF SUMMARY OF THE INVENTION

The present invention (in a first embodiment) relates to a process for the dehydration of an alcohol having at least 2 carbon atoms to make the corresponding olefin, comprising:
introducing in a reactor a stream (A) comprising at least an alcohol, optionally water, optionally an inert component, contacting said stream with a catalyst in said reactor at conditions effective to dehydrate at least a portion of the alcohol to make an olefin,
recovering from said reactor an olefin containing stream (B), Wherein
the catalyst is:
  a crystalline silicate having a ratio Si/Al of at least about 100, or
  a dealuminated crystalline silicate, or
  a phosphorus modified zeolite,
the WHSV of the alcohols is at least 2 $h^{-1}$,
the temperature ranges from 280° C. to 500° C.

The present invention (in a second embodiment) also relates to a process for the dehydration of an alcohol having at least 2 carbon atoms to make the corresponding olefin, comprising:
introducing in a reactor a stream (A) comprising at least an alcohol, optionally water, optionally an inert component, contacting said stream with a catalyst in said reactor at conditions effective to dehydrate at least a portion of the alcohol to make an olefin,
recovering from said reactor an olefin containing stream (B), Wherein
the catalyst is a phosphorus modified zeolite,
the temperature ranges from 280° C. to 500° C.

DETAILED DESCRIPTION OF THE INVENTION

As regards the stream (A), The alcohol is any alcohol provided it can be dehydrated to the corresponding olefin. By way of example mention may be made of alcohols having from 2 to 10 carbon atoms. Advantageously the invention is of interest for ethanol, propanol, butanol and phenylethanol.

The inert component is any component provided there is no adverse effect on the catalyst. Because the dehydration is endothermic the inert component can be used to bring energy. By way of examples the inert component is selected among the saturated hydrocarbons having up to 10 carbon atoms, naphtenes, nitrogen and CO2. Advantageously it is a saturated hydrocarbon or a mixture of saturated hydrocarbons having from 3 to 7 carbon atoms, more advantageously having from 4 to 6 carbon atoms and is preferably pentane. An example of inert component can be any individual saturated compound, a synthetic mixture of the individual saturated compounds as well as some equilibrated refinery streams like straight naphtha, butanes etc. Advantageously the inert component is a saturated hydrocarbon having from 3 to 6 carbon atoms and is preferably pentane. The weight proportions of respectively alcohol, water and inert component are, for example, 5-100/0-95/0-95 (the total being 100). The stream (A) can be liquid or gaseous.

As regards the reactor, it can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. The dehydration may be performed continuously in a fixed bed reactor configuration using a pair of parallel "swing" reactors. The various preferred catalysts of the present invention have been found to exhibit high stability. This enables the dehydration process to be performed continuously in two parallel "swing" reactors wherein when one reactor is operating, the other reactor is undergoing catalyst regeneration. The catalyst of the present invention also can be regenerated several times.

As regards the pressure, it can be any pressure but it is more easy and economical to operate at moderate pressure. By way of example the pressure of the reactor ranges from 0.5 to 30 bars absolute (50 kPa to 3 MPa), advantageously from 0.5 to 5 bars absolute (50 kPa to 0.5 MPa), more advantageously from 1.2 to 5 bars absolute (0.12 MPa to 0.5 MPa) and preferably from 1.2 to 4 bars absolute (0.12 MPa to 0.4 MPa). Advantageously the partial pressure of the alcohol is from 1.2 to 4 bars absolute (0.12 MPa to 0.4 MPa), more advantageously from 1.2 to 3.5 bars absolute (0.35 MPa), preferably from 1.2 to 2 bars absolute (0.12 MPa to 0.2 MPa).

As regards the temperature, it ranges from 280° C. to 500° C., advantageously from 280° C. to 450° C., more advantageously from 300° C. to 400° C. preferably from 330° C. to 380° C.

These reaction temperatures refer substantially to average catalyst bed temperature. The ethanol dehydration is an endothermic reaction and requires the input of reaction heat in order to maintain catalyst activity sufficiently high and shift the thermodynamic equilibrium to sufficiently high conversion levels.

In case of fluidised bed reactors: (i) for stationary fluidised beds without catalyst circulation, the reaction temperature is substantially homogeneous throughout the catalyst bed; (ii) in case of circulating fluidised beds where catalyst circulates between a converting reaction section and a catalyst regeneration section, depending on the degree of catalyst backmixing the temperature in the catalyst bed approaches homogeneous conditions (a lot of backmixing) or approaches plug flow conditions (nearly no backmixing) and hence a decreasing temperature profile will install as the conversion proceeds.

In case of fixed bed or moving bed reactors, a decreasing temperature profile will install as the conversion of the alcohol proceeds. In order to compensate for temperature drop and consequently decreasing catalyst activity or approach to thermodynamic equilibrium, reaction heat can be introduced by using several catalyst beds in series with interheating of the reactor effluent from the first bed to higher temperatures and introducing the heated effluent in a second catalyst bed, etc. When fixed bed reactors are used, a multi-tubular reactor can be used where the catalyst is loaded in small-diameter tubes that are installed in a reactor shell. At the shell side, a heating medium is introduced that provides the required reaction heat by heat-transfer through the wall of the reactor tubes to the catalyst.

As regards the WHSV of the alcohol, it ranges advantageously from 2 to 20 $h^{-1}$, more advantageously from 4 to 20 $h^{-1}$, preferably from 5 to 15 $h^{-1}$, more preferably from 7 to 12 $h^{-1}$.

As regards the stream (B), it comprises essentially water, olefin, the inert component (if any) and unconverted alcohol. Said unconverted alcohol is supposed to be as less as possible. The olefin is recovered by usual fractionation means. Advantageously the inert component, if any, is recycled in the stream (A) as well as the unconverted alcohol, if any. Unconverted alcohol, if any, is recycled to the reactor in the stream (A).

As regards the catalyst and more specifically (i) the crystalline silicate having a ratio Si/Al of at least about 100 or (ii) the dealuminated crystalline silicates, they are containing advantageously at least one 10 members ring into the structure. It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57) and ZSM-48 family of microporous materials consisting of silicon, aluminium, oxygen and optionally boron.

The crystalline silicate having a ratio Si/Al of at least about 100 is advantageously selected among the MFI and the MEL.

Advantageously the crystalline silicate having a ratio Si/Al of at least about 100 and the dealuminated crystalline silicate are essentially in H-form. It means that a minor part (less than about 50%) can carry metallic compensating ions e.g. Na, Mg, Ca, La, Ni, Ce, Zn, Co.

The dealuminated crystalline silicate is advantageously such as about 10% by weight of the aluminium is removed. Such dealumination can be done by any conventional techniques known per se but is advantageously made by a steaming optionally followed by a leaching. The crystalline silicate having a ratio Si/Al of at least about 100 can be synthesized as such or it can be prepared by dealumination of a crystalline silicate at conditions effective to obtain a ratio Si/Al of at least about 100.

The three-letter designations "MFI" and "MEL" each representing a particular crystalline silicate structure type as established by the Structure Commission of the International Zeolite Association. Examples of a crystalline silicate of the MFI type are the synthetic zeolite ZSM-5 and silicalite and other MFI type crystalline silicates known in the art. Examples of a crystalline silicate of the MEL family are the zeolite ZSM-11 and other MEL type crystalline silicates known in the art. Other examples are Boralite D and silicalite-2 as described by the International Zeolite Association (Atlas of zeolite structure types, 1987, Butterworths). The preferred crystalline silicates have pores or channels defined by ten oxygen rings and a high silicon/aluminium atomic ratio.

Crystalline silicates are microporous crystalline inorganic polymers based on a framework of $XO_4$ tetrahedra linked to each other by sharing of oxygen ions, where X may be trivalent (e.g. Al, B, ... ) or tetravalent (e.g. Ge, Si, ... ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bidirectional intersecting pore system with the following pore diameters: a straight channel along [010]: 0.53-0.56 nm and a sinusoidal channel along [100]:0.51-0.55 nm. Crystalline silicates with the MEL structure possess a bidirectional intersecting straight pore system with straight channels along [100] having pore diameters of 0.53-0.54 nm.

In this specification, the term "silicon/aluminium atomic ratio" or "silicon/aluminium ratio" is intended to mean the framework Si/Al atomic ratio of the crystalline silicate. Amorphous Si and/or Al containing species, which could be in the pores are not a part of the framework. As explained hereunder in the course of a dealumination there is amorphous Al remaining in the pores, it has to be excluded from the overall Si/Al atomic ratio. The overall material referred above doesn't include the Si and Al species of the binder.

In a specific embodiment the catalyst has a high silicon/aluminium atomic ratio, of at least about 100, preferably greater than about 150, more preferably greater than about 200, whereby the catalyst has relatively low acidity. The acidity of the catalyst can be determined by the amount of residual ammonia on the catalyst following contact of the catalyst with ammonia which adsorbs to the acid sites on the catalyst with subsequent ammonium desorption at elevated temperature measured by differential thermogravimetric analysis. Preferably, the silicon/aluminium ratio (Si/Al) ranges from about 100 to about 1000, most preferably from about 200 to about 1000. Such catalysts are known per se. "about 100" means that 100 is not a strict ratio but corresponds to a crystalline silicate having an acidity low enough to prevent high catalytic activity in addition to the dehydration to olefin. At a Si/Al ratio above about 100 there is essentially a dehydration to olefin and almost no side reactions which could lead to aldehydes, to saturated hydrocarbons or any undesirable component.

In a specific embodiment the crystalline silicate is steamed to remove aluminium from the crystalline silicate framework. The steam treatment is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100% steam. The steam atmosphere preferably contains from 5 to 100 vol % steam with from 0 to 95 vol % of an inert gas, preferably nitrogen. A more preferred atmosphere comprises 72 vol % steam and 28 vol % nitrogen i.e. 72 kPa steam at a pressure of one atmosphere. The steam treatment is preferably carried out for a period of from 1 to 200 hours, more preferably from 20 hours to 100 hours. As stated above, the steam treatment tends to reduce the amount of tetrahedral aluminium in the crystalline silicate framework, by forming alumina.

In a more specific embodiment the crystalline silicate catalyst is dealuminated by heating the catalyst in steam to remove aluminium from the crystalline silicate framework and extracting aluminium from the catalyst by contacting the catalyst with a complexing agent for aluminium to remove from pores of the framework alumina deposited therein during the steaming step thereby to increase the silicon/aluminium atomic ratio of the catalyst. The catalyst having a high silicon/aluminium atomic ratio for use in the catalytic process of the present invention is manufactured by removing aluminium from a commercially available crystalline silicate. By way of example a typical commercially available silicalite has a silicon/aluminium atomic ratio of around 120. In accordance with the present invention, the commercially available crystalline silicate is modified by a steaming process which reduces the tetrahedral aluminium in the crystalline silicate framework and converts the aluminium atoms into octahedral aluminium in the form of amorphous alumina. Although in the steaming step aluminium atoms are chemically removed from the crystalline silicate framework structure to form alumina particles, those particles cause partial obstruction of the pores or channels in the framework. This could inhibit the dehydration process of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminium complex yields the overall effect of de-alumination of the crystalline silicate. In this way by removing aluminium from the crystalline silicate framework and then removing alumina formed therefrom from the pores, the process aims at achieving a substantially homogeneous de-alumination throughout the whole pore surfaces of the catalyst. This reduces the acidity of the catalyst. The reduction of acidity ideally occurs substantially homogeneously throughout the pores defined in the crystalline silicate framework. Following the steam treatment, the extraction process is performed in order to de-aluminate the catalyst by leaching. The aluminium is preferably extracted from the crystalline silicate by a complexing agent which tends to form a soluble complex with alumina. The complexing agent is preferably in an aqueous solution thereof. The complexing agent may comprise an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The complexing agent may comprise an inorganic acid such as nitric acid, halogenic acids, sulphuric acid, phosphoric acid or salts of such acids or a mixture of such acids. The complexing agent may also comprise a mixture of such organic and inorganic acids or their corresponding salts. The complexing agent for aluminium preferably forms a water-soluble complex with aluminium, and in particular removes alumina which is formed during the steam treatment step from the crystalline silicate. A particularly preferred complexing agent may comprise an amine, preferably ethylene diamine tetraacetic acid (EDTA) or a salt thereof, in particular the sodium salt thereof. In a preferred embodiment, the framework silicon/aluminium ratio is increased by this process to a value of from about 150 to 1000, more preferably at least 200.

Following the aluminium leaching step, the crystalline silicate may be subsequently washed, for example with distilled water, and then dried, preferably at an elevated temperature, for example around 110° C.

Additionally, if during the preparation of the catalysts of the invention alkaline or alkaline earth metals have been used, the molecular sieve might be subjected to an ion-exchange step. Conventionally, ion-exchange is done in aqueous solutions using ammonium salts or inorganic acids.

Following the de-alumination step, the catalyst is thereafter calcined, for example at a temperature of from 400 to 800° C. at atmospheric pressure for a period of from 1 to 10 hours.

In another specific embodiment the crystalline silicate catalyst is mixed with a binder, preferably an inorganic binder, and shaped to a desired shape, e.g. pellets. The binder is selected so as to be resistant to the temperature and other conditions employed in the dehydration process of the invention. The binder is an inorganic material selected from clays, silica, metal silicates, metal oxides such as $ZrO_2$ and/or metals, or gels including mixtures of silica and metal oxides. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica. The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst.

Such a mixture of crystalline silicate and an inorganic oxide binder is referred to as a formulated crystalline silicate. In mixing the catalyst with a binder, the catalyst may be formulated into pellets, extruded into other shapes, or formed into spheres or a spray-dried powder. Typically, the binder and the crystalline silicate catalyst are mixed together by a mixing process. In such a process, the binder, for example silica, in the form of a gel is mixed with the crystalline silicate catalyst material and the resultant mixture is extruded into the desired shape, for example cylindic or multi-lobe bars. Spherical shapes can be made in rotating granulators or by oil-drop technique. Small spheres can further be made by spray-drying a catalyst-binder suspension. Thereafter, the formulated crystalline silicate is calcined in air or an inert gas, typically at a temperature of from 200 to 900° C. for a period of from 1 to 48 hours. The binder preferably does not contain any aluminium compounds, such as alumina. This is because as mentioned above the preferred catalyst for use in the invention is de-aluminated to increase the silicon/aluminium ratio of the crystalline silicate. The presence of alumina in the binder yields other excess alumina if the binding step is performed prior to the aluminium extraction step. If the aluminium-containing binder is mixed with the crystalline silicate catalyst following aluminium extraction, this re-aluminates the catalyst.

In addition, the mixing of the catalyst with the binder may be carried out either before or after the steaming and extraction steps.

In another embodiment the catalyst is a crystalline silicate catalyst having a monoclinic structure, which has been produced by a process comprising providing a crystalline silicate of the MFI-type having a silicon/aluminium atomic ratio lower than 80; treating the crystalline silicate with steam and thereafter leaching aluminium from the zeolite by contact with an aqueous solution of a leachant to provide a silicon/aluminium atomic ratio in the catalyst of at least 180 whereby the catalyst has a monoclinic structure.

Preferably, in the steam treatment step the temperature is from 425 to 870° C., more preferably from 540 to 815° C., and at a water partial pressure of from 13 to 200 kPa.

Preferably, the aluminium is removed by leaching to form an aqueous soluble compound by contacting the zeolite with an aqueous solution of a complexing agent for aluminium which tends to form a soluble complex with alumina.

In accordance with this preferred process for producing monoclinic crystalline silicate, the starting crystalline silicate catalyst of the MFI-type has an orthorhombic symmetry and a relatively low silicon/aluminium atomic ratio which can have been synthesized without any organic template molecule and the final crystalline silicate catalyst has a relatively high silicon/aluminium atomic ratio and monoclinic symmetry as a result of the successive steam treatment and aluminium removal. After the aluminium removal step, the crystalline silicate may be ion exchanged with ammonium ions. It is known in the art that such MFI-type crystalline silicates exhibiting orthorhombic symmetry are in the space group Pnma. The x-ray diffraction diagram of such an orthorhombic structure has one peak at d=around 0.365 nm, d=around 0.305 nm and d=around 0.300 nm (see EP-A-0146524).

The starting crystalline silicate has a silicon/aluminium atomic ratio lower than 80. A typical ZSM-5 catalyst has 3.08 wt % $Al_2O_3$, 0.062 wt % $Na_2O$, and is 100% orthorhombic. Such a catalyst has a silicon/aluminium atomic ratio of 26.9.

The steam treatment step is carried out as explained above. The steam treatment tends to reduce the amount of tetrahedral aluminium in the crystalline silicate framework by forming alumina. The aluminium leaching or extraction step is carried out as explained above. In the aluminium leaching step, the crystalline silicate is immersed in the acidic solution or a solution containing the complexing agent and is then preferably heated, for example heated at reflux conditions (at boiling temperature with total return of condensed vapours), for an extended period of time, for example 18 hours. Following the aluminium leaching step, the crystalline silicate is subsequently washed, for example with distilled water, and then dried, preferably at an elevated temperature, for example around 110° C. Optionally, the crystalline silicate is subjected to ion exchange with ammonium ions, for example by immersing the crystalline silicate in an aqueous solution of $NH_4Cl$.

Finally, the catalyst is calcined at an elevated temperature, for example at a temperature of at least 400° C. The calcination period is typically around 3 hours.

The resultant crystalline silicate has monoclinic symmetry, being in the space group $P2_1/n$. The x-ray diffraction diagram of the monoclinic structure exhibits three doublets at d=around 0.36, 0.31 and 0.19 nm. The presence of such doublets is unique for monoclinic symmetry. More particularly, the doublet at d=around 0.36, comprises two peaks, one at d=0.362 nm and one at d=0.365 nm. In contrast, the orthorhombic structure has a single peak at d=0.365 nm.

The presence of a monoclinic structure can be quantified by comparing the x-ray diffraction line intensity at d=around 0.36 nm. When mixtures of MFI crystalline silicates with pure orthorhombic and pure monoclinic structure are prepared, the composition of the mixtures can be expressed as a monoclinicity index (in %). The x-ray diffraction patterns are recorded and the peak height at d=0.362 nm for monoclinicity and d=0.365 nm for orthorhombicity is measured and are denoted as lm and lo respectively. A linear regression line between the monoclinicity index and the lm/lo gives the relation needed to measure the monoclinicity of unknown samples. Thus the monoclinicity index %=(a×lm/lo-b)×100, where a and b are regression parameters.

The such monoclinic crystalline silicate can be produced having a relatively high silicon/aluminium atomic ratio of at least 100, preferably greater than about 200 preferentially without using an organic template molecule during the crystallisation step. Furthermore, the crystallite size of the monoclinic crystalline silicate can be kept relatively low, typically less than 1 micron, more typically around 0.5 microns, since the starting crystalline silicate has low crystallite size which is not increased by the subsequent process steps. Accordingly, since the crystallite size can be kept relatively small, this can yield a corresponding increase in the activity of the catalyst. This is an advantage over known monoclinic crystalline silicate catalysts where typically the crystallite size is greater than 1 micron as they are produced in presence of an organic template molecule and directly having a high Si/Al ratio which inherently results in larger crystallites sizes.

As regards the phosphorus modified zeolites as a catalyst, they can be prepared based on MFI, MOR, MEL, clinoptilolite or FER crystalline aluminosilicate molecular sieves having an initial Si/Al ratio advantageously between 4 and 500. The P-modified zeolites of this recipe can be obtained based on cheap crystalline silicates with low Si/Al ratio (below 30).

By way of example said P-modified zeolite is made by a process comprising in that order:
selecting a zeolite (advantageously with Si/Al ratio between 4 and 500) among $H^+$ or $NH_4^+$-form of MFI, MEL, FER, MOR, clinoptilolite;
introducing P at conditions effective to introduce advantageously at least 0.05 wt % of P;
separation of the solid from the liquid if any;

an optional washing step or an optional drying step or an optional drying step followed by a washing step;

a calcination step; the catalyst of the XTO and the catalyst of the OCP being the same or different.

The zeolite with low Si/Al ratio has been made previously with or without direct addition of an organic template.

Optionally the process to make said P-modified zeolite comprises the steps of steaming and leaching. The method consists in steaming followed by leaching. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. Nos. 3,911,041, 5,573,990 and 6,797,851.

The catalyst made of a P-modified zeolite can be the P-modified zeolite itself or it can be the P-modified zeolite formulated into a catalyst by combining with other materials that provide additional hardness or catalytic activity to the finished catalyst product.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

Final calcination step is performed advantageously at the temperature 400-700° C. either in a static condition or in a gas flow. Air, nitrogen or any inert gases can be used.

According to a specific embodiment the phosphorous modified zeolite is made by a process comprising in that order:

selecting a zeolite (advantageously with Si/Al ratio between 4 and 500, from 4 to 30 in a specific embodiment) among $H^+$ or $NH_4^+$-form of MFI, MEL, FER, MOR, clinoptilolite;

steaming at a temperature ranging from 400 to 870° C. for 0.01-200 h;

leaching with an aqueous acid solution at conditions effective to remove a substantial part of Al from the zeolite;

introducing P with an aqueous solution containing the source of P at conditions effective to introduce advantageously at least 0.05 wt % of P;

separation of the solid from the liquid;

an optional washing step or an optional drying step or an optional drying step followed by a washing step;

a calcination step.

Optionally between the steaming step and the leaching step there is an intermediate step such as, by way of example, contact with silica powder and drying.

Advantageously the selected MFI, MEL, FER, MOR, clinoptilolite (or $H^+$ or $NH_4^+$-form MFI, MEL, FER, MOR, clinoptilolite) has an initial atomic ratio Si/Al of 100 or lower and from 4 to 30 in a specific embodiment. The conversion to the $H^+$ or $NH_4^+$-form is known per se and is described in U.S. Pat. Nos. 3,911,041 and 5,573,990.

Advantageously the final P-content is at least 0.05 wt % and preferably between 0.3 and 7 w %. Advantageously at least 10% of Al, in respect to parent zeolite MFI, MEL, FER, MOR and clinoptilolite, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

Said P-modified zeolite can be used as itself as a catalyst. In another embodiment it can be formulated into a catalyst by combining with other materials that provide additional hardness or catalytic activity to the finished catalyst product. Materials which can be blended with the P-modified zeolite can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried particles. The amount of P-modified zeolite which is contained in the final catalyst product ranges from 10 to 90 weight percent of the total catalyst, preferably 20 to 70 weight percent of the total catalyst.

As regards the second embodiment which relates to a process for the dehydration of at least an alcohol to make at least an olefin, comprising: introducing in a reactor a stream (A) comprising at least an alcohol, optionally water, optionally an inert component, contacting said stream with a catalyst in said reactor at conditions effective to dehydrate at least a portion of the alcohol to make an olefin,
recovering from said reactor an olefin containing stream (B), Wherein
the catalyst is a phosphorus modified zeolite,
the temperature ranges from 280° C. to 500° C.,
the detailed description is the same as above except the WHSV.

The WHSV of the alcohol ranges advantageously from 0.1 to 20 h$^{-1}$, more advantageously from 0.5 to 20 h$^{-1}$, preferably from 0.5 to 15 h$^{-1}$, more preferably from 0.7 to 12 h$^{-1}$.

The detailed description of the first embodiment are available mutadis mutandis to the second embodiment.

One skilled in the art will also appreciate that the olefins made by the dehydration process of the present invention can be, by way of example, polymerized. When the olefin is ethylene it can be, by way of example, polymerized to form polyethylenes,
dimerized to butene and then isomerised to isobutene, said isobutene reacting with ethanol to produce ETBE,
dimerised to 1-butene, trimerised to 1-hexene or tetramerised to 1-octene, said alpha-olefins comonomers are further reacted with ethylene to produce polyethylene
dimerised to 1-butene, said 1-butene is isomerised to 2-butene and said 2-butene is further converted with ethylene by metathesis reaction into propylene and said propylene can be polymerised to polypropylene,
converted to ethylene oxide and glycol or
converted to vinyl chloride.

The present invention relates also to said polyethylenes, polypropylene, propylene, butene, hexane, octene, isobutene, ETBE, vinyl chloride, ethylene oxide and glycol.

EXAMPLES

The stainless-steel reactor tube has an internal diameter of 10 mm. 10 ml of catalyst, as pellets of 35-45 mesh, is loaded in the tubular reactor. The void spaces before and after the catalyst are filled with SiC granulated of 2 mm. The temperature profile is monitored with the aid of a thermocouple well placed inside the reactor. The reactor temperature is increased at a rate of 60° C./h to 550° C. under air, kept 2 hours at 550° C. and then purged by nitrogen. The nitrogen is then replaced by the feed (either a pure ethanol feed or an aqueous ethanol feed). The catalytic tests are then performed down-flow, at near atmospheric pressure (pressure of 1.35 bara), in a temperature range of 300-450° C. and with a weight hour space velocity (WHSV) varying from 2 to 10 h$^{-1}$. Analysis of the products is performed by using an on-line gas chromatograph.

Example 1 (Comparative)

γ-Al$_2$O$_3$

A γ-Al$_2$O$_3$ as 1.5 mm extrudates exhibits the following textural properties: a specific surface area of 285 m$^2$/g, with a porous distribution centered around 94 Å, and a porous volume of 0.67 ml/g. The impurities present on the alumina in small amounts are summarized below:
0.51% wt S, 0.4% wt Si, 0.04% wt Ca, 0.08% wt Cl, 0.02% wt Fe, 0.01% wt Cu.

Figure 2:
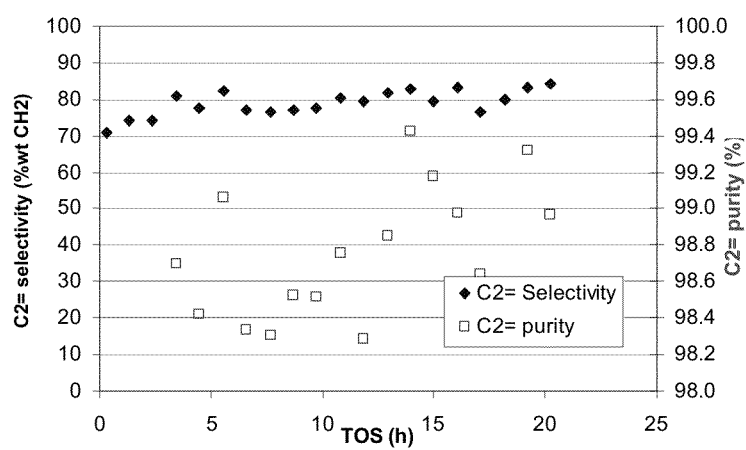
Figure 3:
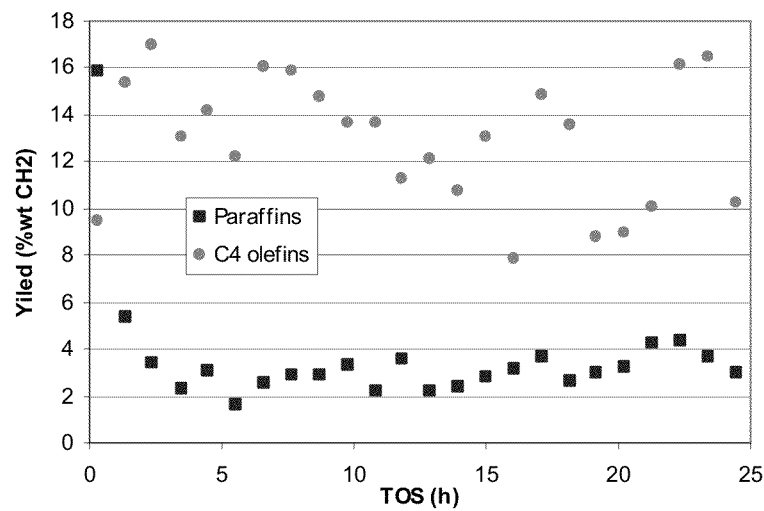

Catalyst Performances:
For the following experiments, a pure ethanol feed has been used.
At 400° C., under 1.35 bara and with an ethanol space velocity of 1.8 h$^{-1}$, the ethanol conversion is almost complete (>99.7% wt), with a $C_2^=$ selectivity of 80% wt (CH$_2$ basis) and a $C_2^=$ purity remaining above 98.2% wt.
The limited $C_2^=$ selectivity can be explained by the fact that under these operating conditions, the formation of heavier compounds takes place, especially up to 12% wt (CH$_2$ basis) of $C_4^=$ olefins and around 3% wt paraffins (CH$_2$ basis).
The results are displayed on FIG. 1-3:
FIG. 1—Ethanol conversion and $C_2^=$ yield (wt CH$_2$ basis) as a function of TOS (Time On Stream) (h); 400° C.-1.35 bara-WHSV (EtOH)=1.8 h$^{-1}$
FIG. 2—$C_2^=$ selectivity (wt CH$_2$ basis) and purity as a function of TOS (h); 400° C.-1.35 bara-WHSV (EtOH)=1.8 h$^{-1}$
FIG. 3—$C_4^=$ olefin and paraffin yield (wt CH$_2$ basis) as a function of TOS (h); 400° C.-1.35 bara-WHSV (EtOH)=1.8 h$^{-1}$ The use of this γ-Al$_2$O$_3$ did not allow reaching good performances for ethylene dehydration. Without being bonded by any explanation the inventors think it could be linked to a broad non-ideal distribution of acid sites and to the low purity of the alumina used (sulfur, silicon, iron contents especially are quite high).

Example 2 (Comparative)

Silica-Alumina

The silica-alumina under powder form exhibits a specific area of 377 m$^2$/g, and consists in 94.4% wt Al$_2$O$_3$ and 5.6% wt SiO$_2$.

The catalyst has been first calcined at 600° C. during 2 hours under air before being loaded.

Figure 4:
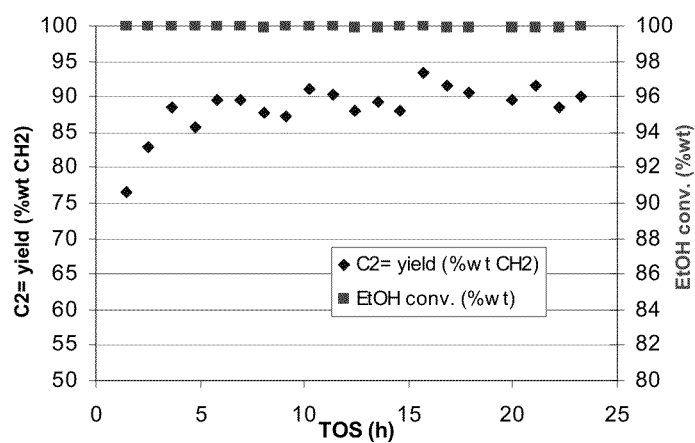
Figure 5:
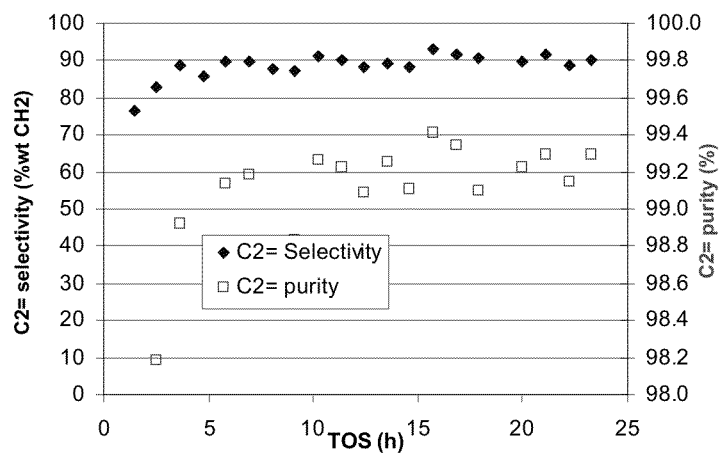
Figure 6:
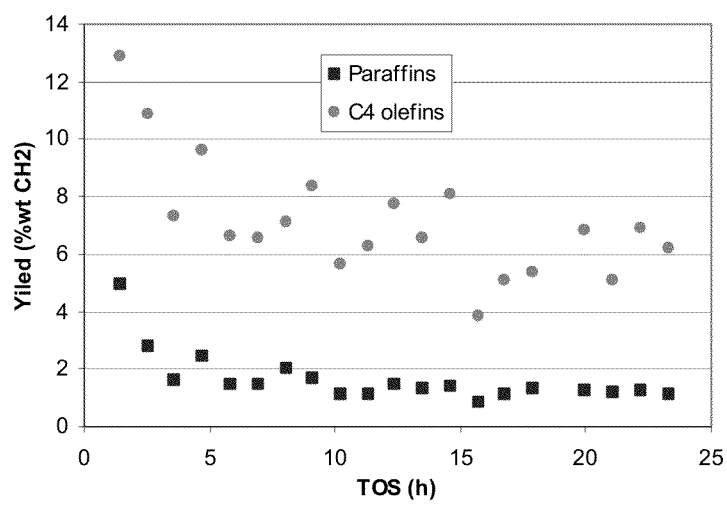
Figure 7:
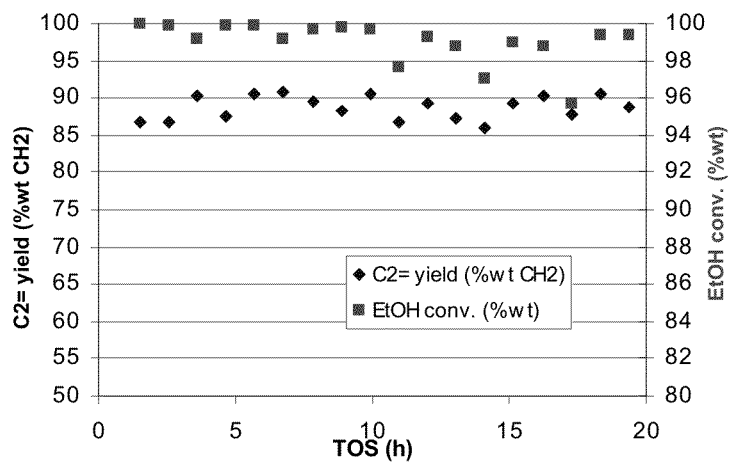
Figure 8:
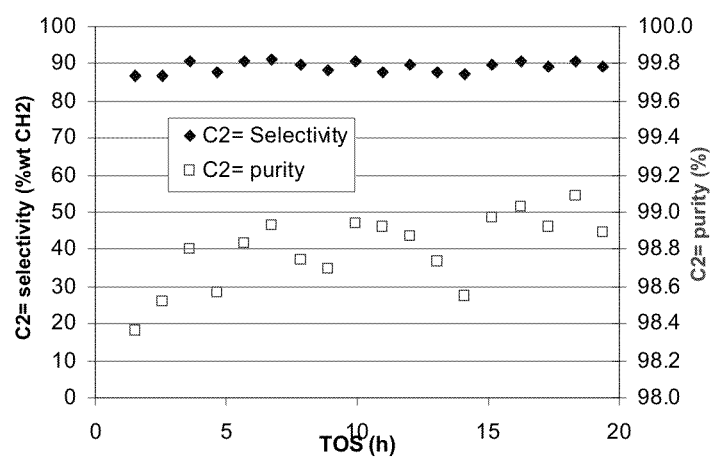
Figure 9:
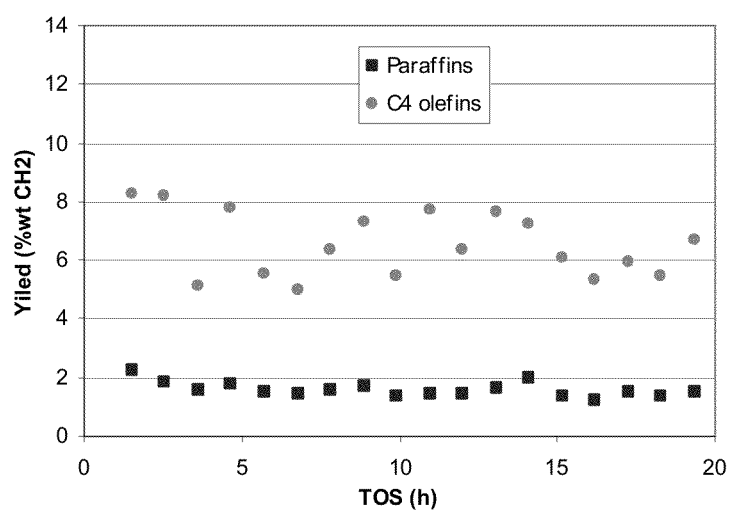

Catalyst Performances:
For the following experiments, a pure ethanol feed has been used.
At 400° C., under 1.35 bara and with an ethanol space velocity of 2.8 h$^{-1}$, the ethanol conversion is almost complete (>99.9% wt), with a $C_2^=$ selectivity of 90% wt (CH$_2$ basis) and a $C_2^=$ purity remaining above 99% wt.
Compared to γ-Al$_2$O$_3$, better performances are achieved in terms of selectivity and purity. But this time again, the amount of $C_4^=$ olefins remains quite high (~6% wt (CH$_2$ basis) $C_4^=$).
The results are displayed on FIG. 4-6
FIG. 4—Ethanol conversion and $C_2^=$ yield (wt CH$_2$ basis) as a function of TOS (h); 400° C.-1.35 bara-WHSV (EtOH)=2.8 h$^{-1}$
FIG. 5—$C_2^=$ selectivity (wt CH$_2$ basis) and purity as a function of TOS (h); 400° C.-1.35 bara-WHSV (EtOH)=2.8 h$^{-1}$
FIG. 6—C4=olefin and paraffin yield (wt CH2 basis) as a function of TOS (h); 400° C.-1.35 bara-WHSV (EtOH)=2.8 h$^{-1}$
Another set of operating conditions were then used in order to limit the formation of $C_4^+$ compounds: the space velocity of ethanol was increased up to 5 h$^{-1}$.
The C, H, N analysis of the spent catalyst at the end of the test reveals a carbon content of 5.2% wt indicating that coking occurs in that case also in quite a large extent, while simultaneously, the formation of heavies decreases slightly.
The results are displayed on FIG. 7-9
FIG. 7—Ethanol conversion and C2=yield (wt CH2 basis) as a function of TOS (h); 400° C.-1.35 bara-WHSV (EtOH)=5 h$^{-1}$ FIG. 8—C2=selectivity (wt CH2 basis) and purity as a function of TOS (h); 400° C.-1.35 bara-WHSV (EtOH)=5 h$^{-1}$ FIG. 9—C4=olefin and paraffin yield (wt CH2 basis) as a function of TOS (h); 400° C.-1.35 bara-WHSV (EtOH)=5 h$^{-1}$ The use of a silica-alumina catalyst, allows to reach better catalytic performances for ethylene dehydration than gamma alumina. However, it is interesting to note that despite a quite important formation of heavy compounds ($C_4^+$) at moderate space velocity (2.8 h$^{-1}$), an increase of the ethanol flow rate does not allow to improve the catalytic performances towards ethylene dehydration:ethanol conversion is no more complete.

Example 3 (According to the Invention)

The silicalite used here is a zeolite H-ZSM-5 with a pure MFI structure having a Si/Al of 169 under powder form.

Catalyst performances: For the following experiments, a pure ethanol feed has been used at 350° C., under 1.35 bara and with an ethanol space velocity of up to 10 h$^{-1}$.

In this set of operating conditions, ethanol conversion is almost complete (>98.8% wt), with a $C_2^=$ selectivity of 96% wt ($CH_2$ basis) and a $C_2^=$ purity remaining above 99.8% wt. Ethanol dehydration is the main reaction, as the temperature profile follow-up may testify it.

Very low amounts of $C_4^=$, $C_3^=$ and aromatics are now formed (0.9% wt, 0.7% wt and 0.2% wt ($CH_2$ basis) respectively).

Figure 10:
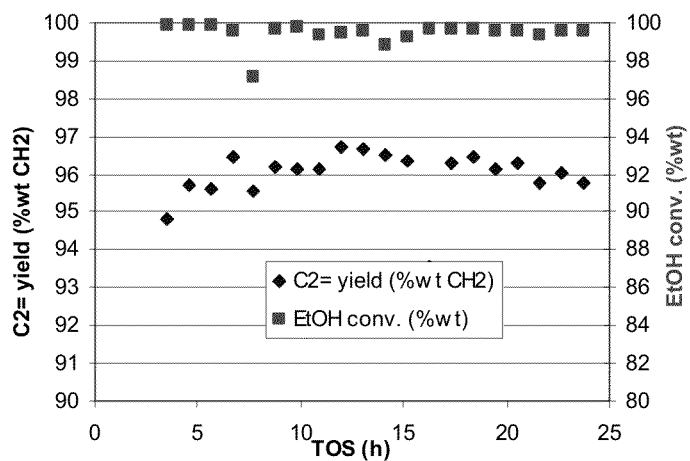
Figure 11:
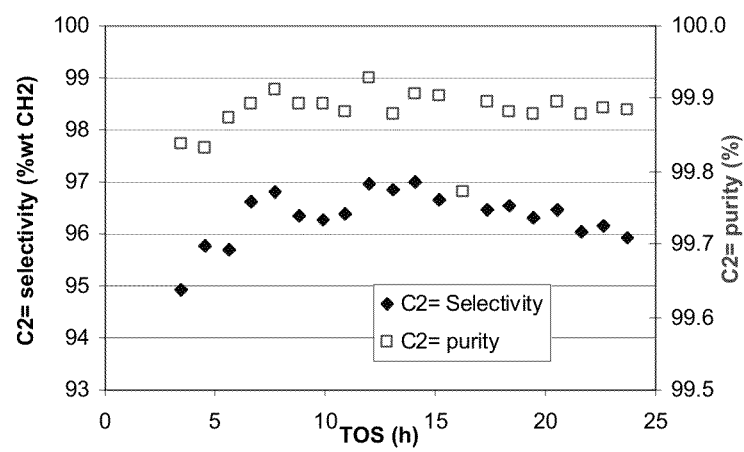
Figure 12:
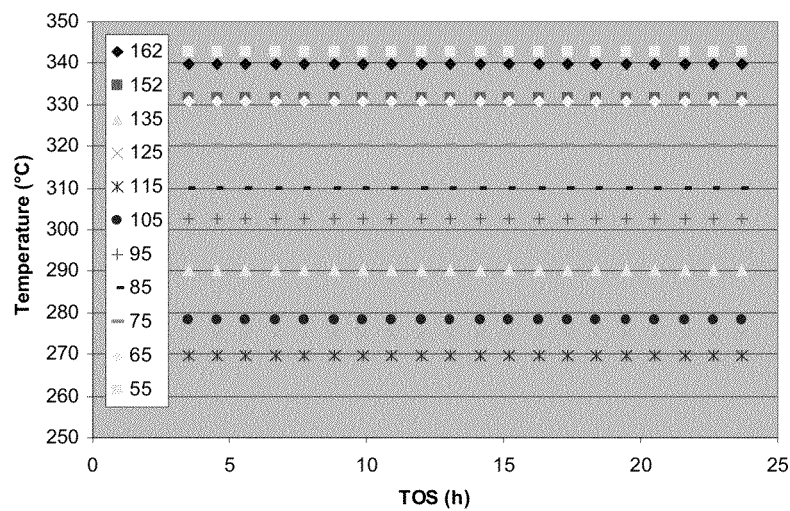

The results are displayed on FIG. 10-12

FIG. 10—Ethanol conversion and C2=yield (wt CH2 basis) as a function of TOS (h); 350° C.-1.35 bara-WHSV (EtOH)=10 h$^{-1}$ FIG. 11—C2=selectivity (wt CH2 basis) and purity as a function of TOS (h); 350° C.-1.35 bara-WHSV (EtOH)=10 h$^{-1}$ FIG. 12—Temperature profile along the catalytic bed as a function of TOS (h); 350° C.-1.35 bara-WHSV (EtOH)=10 h$^{-1}$ the legend indicates the height at which the measurement is performed, the top of the bed being located at 162 mm and the bottom of the bed corresponding to 55 mm.

To check the impact of the feed, an aqueous ethanol has been used as a feed stock (95/5% wt EtOH/$H_2O$).

The graphs reported below indicate that the presence of water even allows an improvement of $C_2^=$ selectivity, reaching 98% wt ($CH_2$ basis), ethanol conversion being around 98% wt. A further decrease of temperature down to 300° C., did not allow to recover better results.

Figure 13:
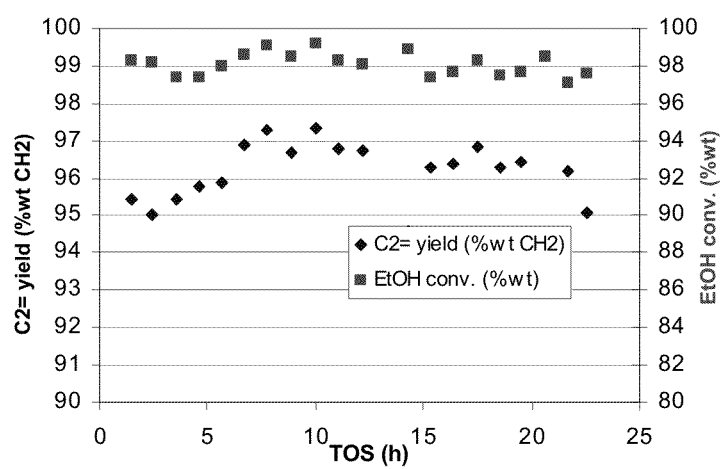
Figure 14:
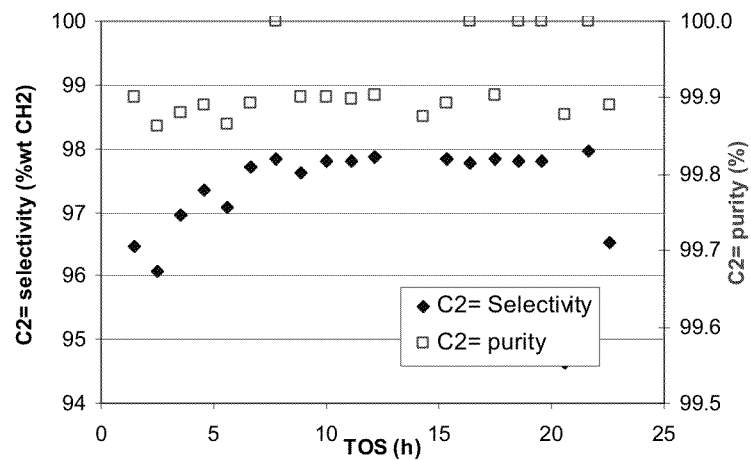

The results are displayed on FIG. 13-14

FIG. 13—Ethanol conversion and C2=yield (wt CH2 basis) as a function of TOS (h); 350° C.-1.35 bara-WHSV (EtOH)=10 h$^{-1}$ (95/5) % wt EtOH/H2O mixture.

FIG. 14—C2=selectivity (wt CH2 basis) and purity as a function of TOS (h); 350° C.-1.35 bara-WHSV (EtOH)=10 h$^{-1}$ (95/5) % wt EtOH/H2O mixture.

The use of a high Si/Al silicalite allows to get very good catalytic performances for ethylene dehydration:ethanol conversion is almost complete (>98.8% wt), with a $C_2^=$ selectivity of 96% wt ($CH_2$ basis) and a $C_2^=$ purity remaining above 99.8% wt. It is worth also to underline that such results are obtained in a high space velocity range (10 h$^{-1}$): this could allow to increase the reactor throughput significantly. Furthermore, the use of aqueous ethanol (mixture of 95-5% wt EtOH—$H_2O$) leads to an improvement of $C_2^=$ selectivity, though a slight decrease of ethanol conversion down to 98% wt, is noticed.

Example 4 (According to the Invention)

The catalyst is a shaped cylinder catalyst containing 30% wt of binder (silica) and 70% wt of silicalite (MFI), which has been steamed and acid exchanged, leading to an overall Si/Al of around 250.

Catalyst performances: By comparison with example 3 the operating conditions were set as follows: temperature was kept at 350° C., and the weight hourly space velocity decreased to 7 h$^{-1}$, pressure being kept the same, and pure ethanol being used as the feed. In these operating conditions, ethanol conversion is very high (>97% wt), with a $C_2^=$ selectivity of 98% wt ($CH_2$ basis) and a $C_2^=$ purity remaining above 99.8% wt. Ethanol dehydration is the main reaction, as the temperature profile follow-up may testify it.

The results are displayed on FIG. 15-18

Figure 15:
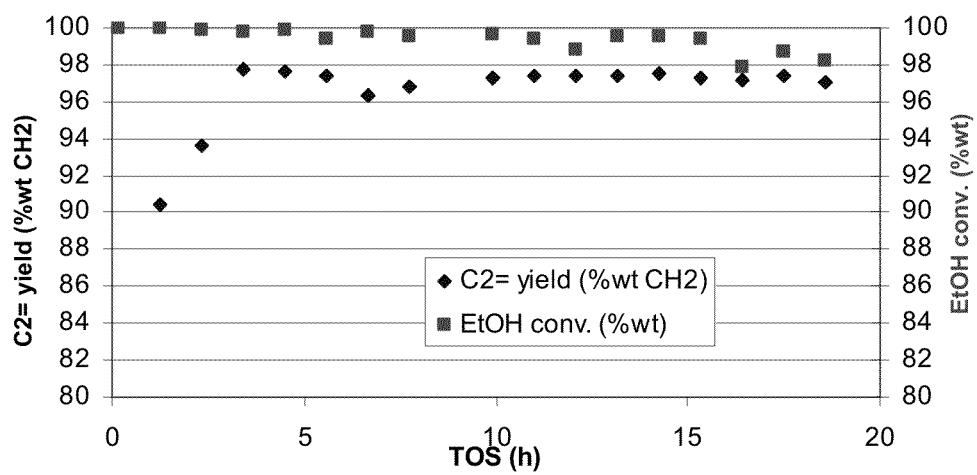
Figure 16:
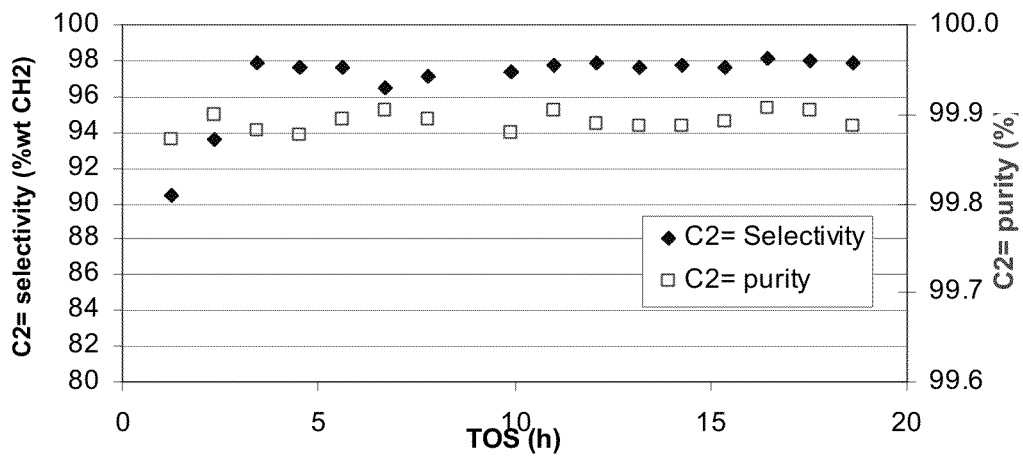
Figure 17:
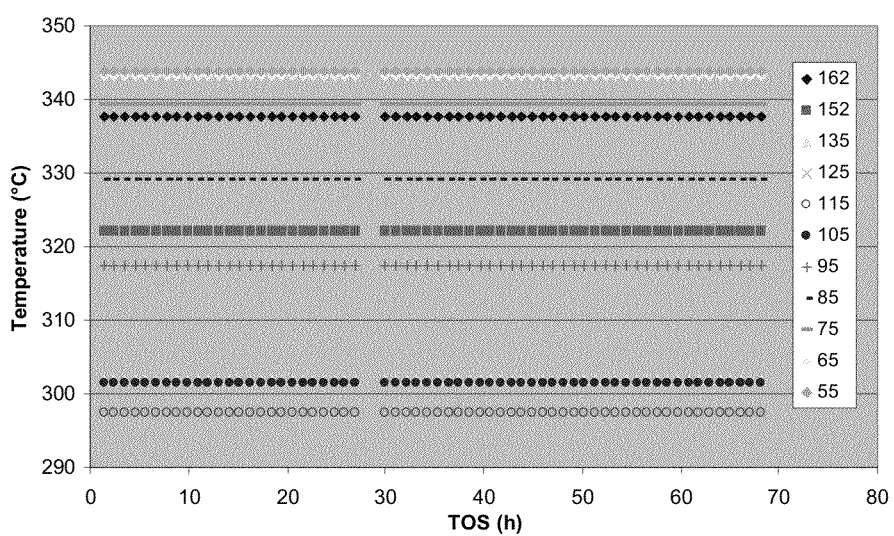

FIG. 15—Ethanol conversion and C2=yield (wt CH2 basis) as a function of TOS (h); 350° C.-1.35 bara-WHSV (EtOH)=7 h$^{-1}$ FIG. 16—C2=selectivity (wt CH2 basis) and purity as a function of TOS (h); 350° C.-1.35 bara-WHSV (EtOH)=7 h$^{-1}$ FIG. 17—Temperature profile along the catalytic bed as a function of TOS (h); 350° C.-1.35 bara-WHSV (EtOH)=7 h$^{-1}$, the legend indicates the height at which the measurement is performed, the top of the bed being located at 162 mm and the bottom of the bed corresponding to 55 mm.

Figure 18:
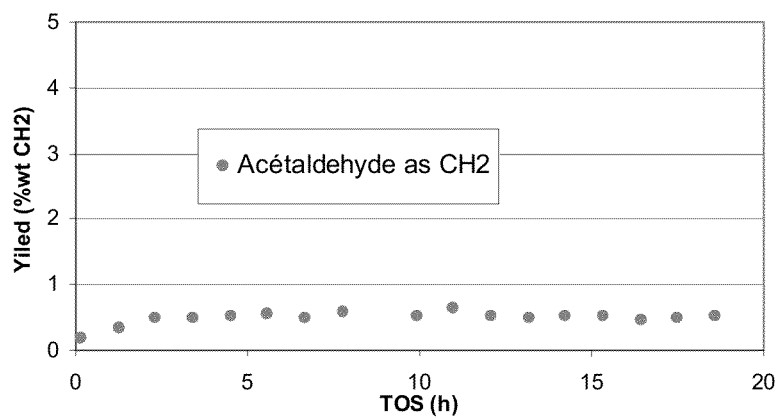
Figure 19:
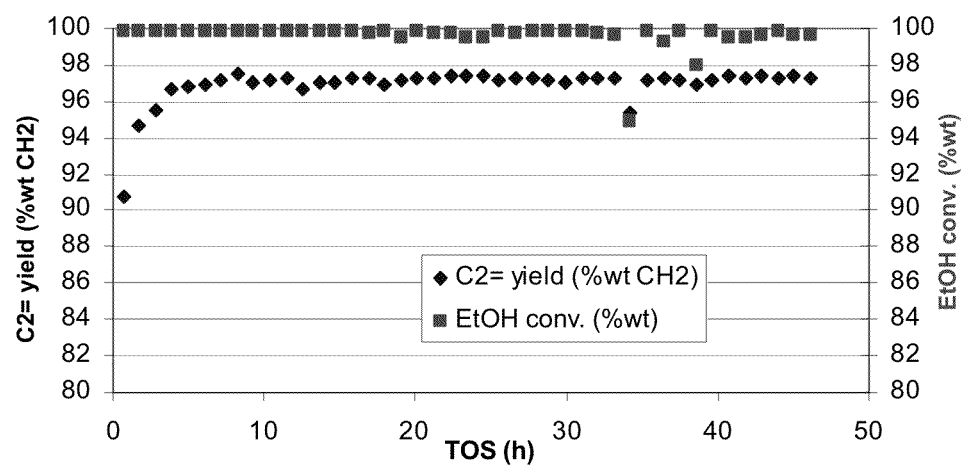
Figure 20:
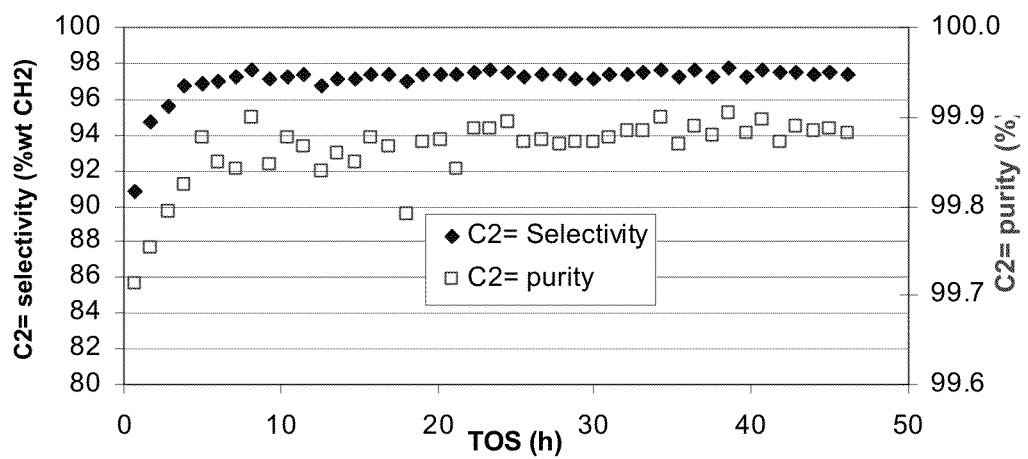
Figure 21:
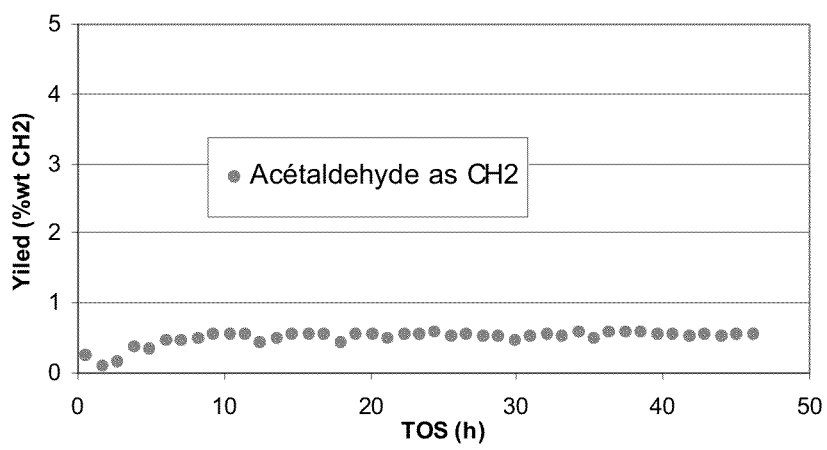
Figure 22:
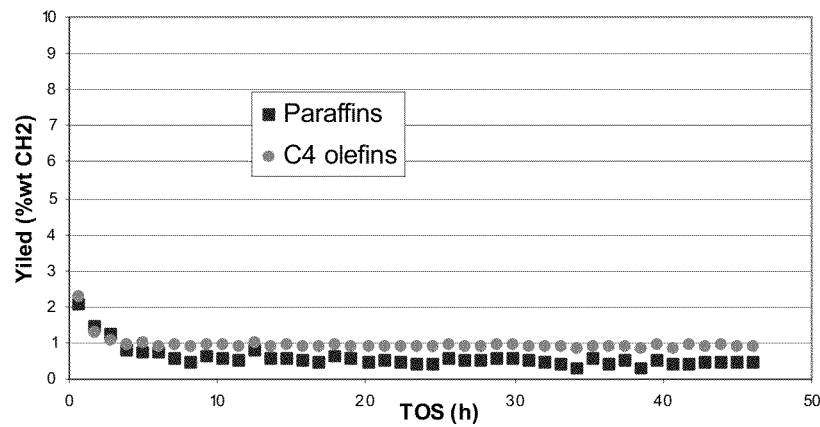
Figure 23:
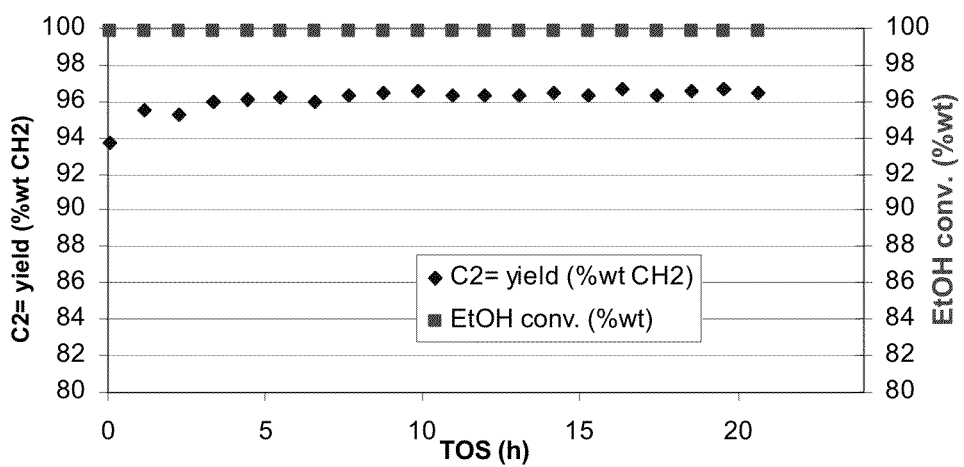
Figure 24:
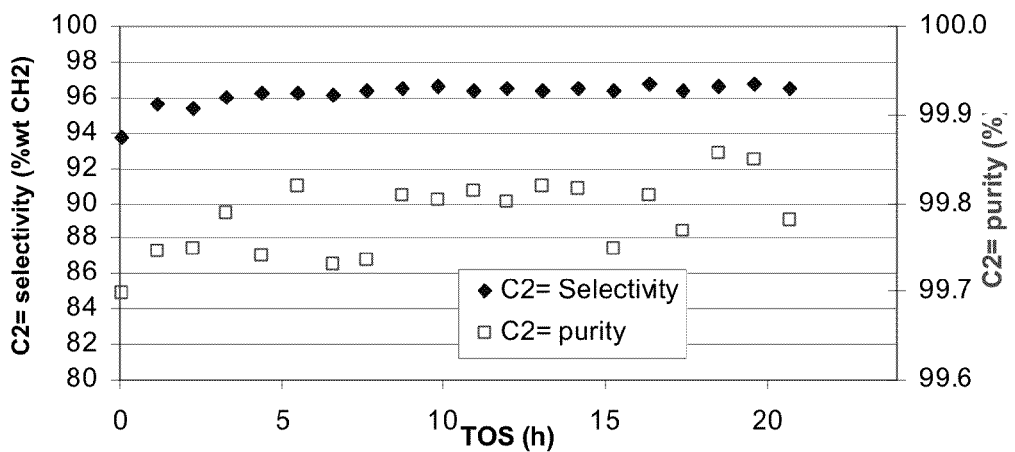
Figure 25:
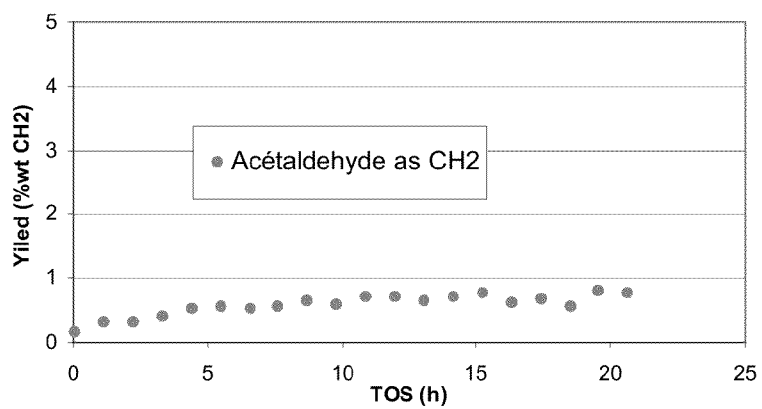
Figure 26:
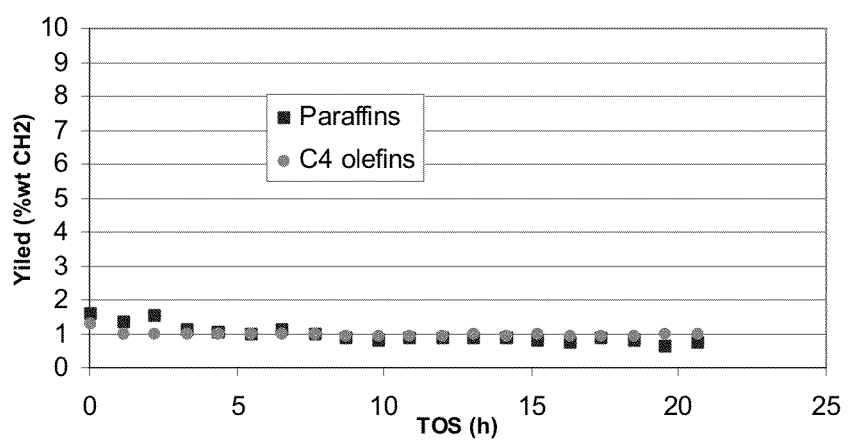

FIG. 18—acetaldehyde (wt CH2 basis) as a function of TOS (h); 350° C.-1.35 bara-WHSV (EtOH)=7 h$^{-1}$ An other other set of dehydrations was carried out with the same conditions on the same catalyst but the WHSV is lowered to 5 h$^{-1}$. The results are displayed on FIG. 19-22.

Example 5 (According to the Invention)

The catalyst is the same as in ex 4: a shaped cylinder catalyst containing 30% wt of binder (silica) and 70% wt of silicalite (MFI), which has been steamed and acid exchanged, leading to an overall Si/Al of around 250.

Operating conditions: For the following experiments, a pure ethanol feed has been used at 350° C., under 1.35 bara and with an ethanol space velocity of 2 h$^{-1}$. The results are displayed on FIG. 23-26.

Example 6 (According to the Invention, Phosphated Zeolite)

A sample of zeolite ZSM-5 (Si/Al=13) in H-form was steamed at 550° C. for 6 h in 100% $H_2O$. The steamed solid was subjected to a contact with 3.14M solution of $H_3PO_4$ for 4 h under reflux condition (4.2 ml/1 g pf zeolite). Then the solid was separated from the liquid phase by filtering at room temperature. Obtained material was dried at 200° C. for 16 h. 320 g of the dried sample was extruded with a 235 g of low sodium silica sol containing 34 wt % of $SiO_2$, 400 g of specific binder, 165 ml of $H_2O$ and 2-3 wt % of extrusion additives. The extruded solid was dried at room temperature for 24 h followed by drying at 200° C. for 16 h in the oven. The dried extruded catalyst was subjected in a contact with water solution at room temperature for 1 h under stirring followed by filtering drying at 110° C. and calcinations at 700° C. for 2 h.

The specific binder for this example was prepared by blending of equal weight amount of xonotlite and of (NH4)$H_2PO4$ in water solution (1 g xonotlite/4 ml H2O) at room temperature followed by stirring for 1 h, filtering, drying at 110° C. for 16 h and calcinations at 400° C. for 3 h.

Operating conditions: Catalyst tests were performed on 10 ml (6.5 g) of catalyst grains (35-45 meshes) loaded in a tubular reactor with internal diameter 11 mm. Ethanol based blended feed containing 67 wt % of water has been used at 400° C., under 2 bara and with an ethanol space velocity of 7 $h^{-1}$. The results are given in the table 1. The catalyst showed a stable activity at least for 50 h on stream.

TABLE 1

| FEED | 33 wt % EtOH + 67 wt % $H_2O$ |
|---|---|
| EtOH conversion to hydrocarbons (HC), % | 99.8 |
| EtOH conversion to oxygenates, % | 0.1 |
| HC composition, % | |
| Purity in C2's fraction, % | 99.95 |
| Ethylene | 99.00 |
| Ethane | 0.05 |
| Propylene | 0.05 |
| C4+ | 0.52 |
| Unknown | 0.18 |

The invention claimed is:

1. A process for the dehydration of an alcohol having at least 2 carbon atoms to produce a corresponding olefin comprising:
    forming a catalyst comprising a phosphorous modified zeolite by:
    selecting a zeolite with an Si/Al ratio between 4 and 30 from an $H^+$ or $NH_4^+$ form of MFI, MEL, FER, MOR, or clinoptilolite;
    steaming the zeolite at a temperature ranging from 400 to 870° C. for 0.01 to 200 hours;
    leaching the zeolite at conditions effective to remove at least 10% of Al from the zeolite;
    introducing P at conditions effective to introduce at least 0.05 wt % of P;
    separating solids from liquids; and
    calcining;
    introducing a first stream into a reactor, wherein the first stream comprises an alcohol;
    contacting the first stream with the catalyst in the reactor at conditions effective to dehydrate at least a portion of the alcohol to produce an olefin; and
    recovering from the reactor a second stream comprising an olefin;
    wherein the reactor is operated under conditions comprising an alcohol WHSV of at least 2 $h^{-1}$ and temperatures ranging from 280 to 500° C.

2. The process of claim 1, wherein the first stream comprises water.

3. The process of claim 1, wherein the first stream comprises an inert component.

4. The process of claim 1, wherein the alcohol WHSV ranges from 2 to 20 $h^{-1}$.

5. The process of claim 1, wherein the alcohol WHSV ranges from 4 to 20 $h^{-1}$.

6. The process of claim 1, wherein the reactor is operated under pressures ranging from 0.05 to 3 MPa.

7. The process of claim 1, wherein the alcohol in the reactor has a partial pressure ranging from 0.12 to 0.4 MPa.

8. The process of claim 1, wherein the alcohol in the reactor has a partial pressure ranging from 0.12 to 0.2 MPa.

9. The process of claim 1, wherein the temperature of the reactor ranges from 300 to 400° C.

10. The process of claim 1, wherein the alcohol is selected from the group consisting of ethanol, propanol, butanol, phenylethanol, and combinations thereof.

11. The process of claim 1, further comprising, prior to introducing P, steaming the zeolite followed by leaching the zeolite with an aqueous acid solution.

12. The process of claim 1, wherein the zeolite is steamed at a temperature ranging from 480 to 760° C. for 0.01 to 200 hours.

* * * * *